US012629462B2

(12) United States Patent
Krivitski et al.

(10) Patent No.: US 12,629,462 B2
(45) Date of Patent: \*May 19, 2026

(54) CALCULATING CARDIAC OUTPUT OF A PATIENT UNDERGOING VENO-VENOUS EXTRACORPOREAL BLOOD OXYGENATION

(71) Applicant: Transonic Systems Inc., Ithaca, NY (US)

(72) Inventors: Nikolai M. Krivitski, Ithaca, NY (US); Gregory Galyanov, Ithaca, NY (US)

(73) Assignee: Transonic Systems Inc., Ithaca, NY (US)

( \* ) Notice: Subject to any disclaimer, the term of this patent is extended or adjusted under 35 U.S.C. 154(b) by 236 days.

This patent is subject to a terminal disclaimer.

(21) Appl. No.: 18/138,278

(22) Filed: Apr. 24, 2023

(65) Prior Publication Data

US 2023/0256147 A1 Aug. 17, 2023

Related U.S. Application Data

(63) Continuation of application No. 16/864,275, filed on May 1, 2020, now Pat. No. 11,654,218.

(Continued)

(51) Int. Cl.
*A61M 1/16* (2006.01)
*A61M 1/36* (2006.01)

(52) U.S. Cl.
CPC ........ *A61M 1/1603* (2014.02); *A61M 1/1698* (2013.01); *A61M 1/3623* (2022.05);
(Continued)

(58) Field of Classification Search
CPC .............. A61M 1/1603; A61M 1/1698; A61M 1/3623; A61M 2205/3334;
(Continued)

(56) References Cited

U.S. PATENT DOCUMENTS

| | | | |
|---|---|---|---|
| 5,092,357 A | 3/1992 | Chapman et al. | |
| 5,267,417 A | 12/1993 | Rose | |

(Continued)

FOREIGN PATENT DOCUMENTS

| | | |
|---|---|---|
| JP | S60-253457 A | 12/1985 |
| JP | 2008538934 A | 11/2008 |

(Continued)

OTHER PUBLICATIONS

Abrams et al. (2015) "Identification and management of recirculation in venovenous ECMO," Extracorporeal Life Support Organization (ELSO): 1-7.

(Continued)

*Primary Examiner* — Philip R Wiest
(74) *Attorney, Agent, or Firm* — Harter Secrest & Emery LLP; Jodi A. Reynolds, Esq.

(57) ABSTRACT

A system for calculating cardiac output of a patient on an extracorporeal blood oxygenation circuit, such as venovenous extracorporeal membrane oxygenation, includes determining (i) a first arterial carbon dioxide content or surrogate and (ii) a first carbon dioxide content or surrogate in the blood delivered to the patient after passing the oxygenator corresponding to the first removal rate of carbon dioxide from the blood; establishing a second removal rate of carbon dioxide from the blood in the oxygenator in the extracorporeal blood oxygenation circuit; determining (i) a second arterial carbon dioxide content or surrogate and (ii) a second carbon dioxide content or surrogate in the blood delivered to the patient after passing the oxygenator corresponding to the second removal rate of carbon dioxide from the blood; and calculating a cardiac output of the patient corresponding to a blood flow rate through the extracorporeal blood oxygenation circuit, the first arterial carbon dioxide content or surrogate, the first carbon dioxide content (Continued)

or surrogate in the blood delivered to the patient after passing the oxygenator corresponding to the first removal rate of carbon dioxide from the blood; the second arterial carbon dioxide content or surrogate and the second carbon dioxide content or surrogate in the blood delivered to the patient after passing the oxygenator corresponding to the second removal rate of carbon dioxide from the blood.

10 Claims, 3 Drawing Sheets

Related U.S. Application Data

(60) Provisional application No. 62/842,192, filed on May 2, 2019.

(52) U.S. Cl.
CPC . *A61M 2205/3334* (2013.01); *A61M 2205/50* (2013.01); *A61M 2230/04* (2013.01); *A61M 2230/20* (2013.01)

(58) Field of Classification Search
CPC .......... A61M 2230/02; A61M 2230/20; A61M 2230/202; A61B 5/029; A61B 5/14503; A61B 5/14542; A61B 5/6866
See application file for complete search history.

(56) References Cited

U.S. PATENT DOCUMENTS

| | | | |
|---|---|---|---|
| 5,398,461 A | 3/1995 | Rose | |
| 5,437,296 A | 8/1995 | Citino | |
| 5,474,097 A | 12/1995 | Lowe et al. | |
| 5,685,989 A | 11/1997 | Krivitski et al. | |
| 5,928,180 A | 7/1999 | Krivitski et al. | |
| 6,090,061 A | 7/2000 | Steuer et al. | |
| 6,155,984 A | 12/2000 | Krivitski | |
| 6,461,231 B1 | 10/2002 | Taylor et al. | |
| 6,506,146 B1 | 1/2003 | Mohl | |
| 6,616,615 B2 | 9/2003 | Mault | |
| 11,439,735 B2 | 9/2022 | Krivitski et al. | |
| 11,446,438 B2 | 9/2022 | Sowb | |
| 11,654,218 B2 * | 5/2023 | Krivitski ................ | A61B 5/029 604/6.11 |
| 2002/0022785 A1 | 2/2002 | Romano | |
| 2004/0158133 A1 | 8/2004 | Krivitski et al. | |
| 2006/0052715 A1 | 3/2006 | Krivitski et al. | |
| 2006/0211947 A1 | 9/2006 | Krivitski et al. | |
| 2008/0033314 A1* | 2/2008 | Krivitski .............. | A61B 5/0275 600/526 |
| 2009/0043171 A1 | 2/2009 | Rule | |
| 2010/0057046 A1 | 3/2010 | Stevens et al. | |
| 2010/0087046 A1 | 4/2010 | Stevens et al. | |
| 2011/0129389 A1 | 6/2011 | Brady et al. | |
| 2013/0066173 A1 | 3/2013 | Addison et al. | |
| 2013/0310669 A1 | 11/2013 | Kreutz | |
| 2014/0276071 A1 | 9/2014 | Hunziker et al. | |
| 2015/0031969 A1 | 1/2015 | Khair | |
| 2015/0314059 A1 | 11/2015 | Federspiel et al. | |
| 2015/0316404 A1 | 11/2015 | Krivitski et al. | |
| 2016/0000989 A1 | 1/2016 | Haag et al. | |
| 2016/0022524 A1 | 1/2016 | Flake et al. | |
| 2016/0346448 A1 | 12/2016 | Kaiser et al. | |
| 2017/0239407 A1 | 8/2017 | Hayward | |
| 2017/0281063 A1 | 10/2017 | Utsugida et al. | |
| 2018/0353680 A1 | 12/2018 | Al Hatib et al. | |
| 2019/0030232 A1 | 1/2019 | Kreymann et al. | |
| 2019/0083694 A1 | 3/2019 | Kopperschmidt et al. | |

| | | | |
|---|---|---|---|
| 2019/0083789 A1 | 3/2019 | Thakur et al. | |
| 2019/0314567 A1 | 10/2019 | Straube et al. | |
| 2020/0237992 A1 | 7/2020 | Krivitski et al. | |
| 2020/0306437 A1 | 10/2020 | Sternby et al. | |

FOREIGN PATENT DOCUMENTS

| | | |
|---|---|---|
| JP | 2015529116 A | 10/2015 |
| JP | 2017217296 A | 12/2017 |
| WO | 2006096758 A2 | 9/2006 |
| WO | 2006096758 A3 | 9/2006 |

OTHER PUBLICATIONS

Bachmann et al. (2020) "Gas exchange calculation may estimate changes in pulmonary blood flow during veno-arterial extracorporeal membrane oxygenation in a porcine model," American Journal of Physiology-Lung Cellular and Molecular Physiology 318(6): 1-41.
Broman et al. (2015) "Recirculation During Veno-Venous Extra-Corporeal Membrane Oxygenation—A Simulation Study," The International Journal of Artificial Organs 38(1): 23-30.
European Patent Office, Extended European Search Report issued in corresponding European Patent Application No. 20744707.9, dated Apr. 7, 2022.
European Patent Office, Extended European Search Report issued in corresponding European Patent Application No. 20798353.7, dated Jan. 5, 2023.
Joyce et al. (2018) "A mathematical model of CO2, 02 and N2 exchange during venovenous extracorporeal membrane oxygenation," Intensive Care Medicine Experimental 6(25): 1-13.
Korean Intellectual Property Office (ISA/KR), International Search Report issued in corresponding International Application No. PCT/US/2020/015016, dated May 27, 2020.
Korean Intellectual Property Office (ISA/KR), International Search Report issued in corresponding International Application No. PCT/US/2020/015666, dated May 26, 2020.
Korean Intellectual Property Office (ISA/KR), International Search Report issued in corresponding International Application No. PCT/US/2020/030916, mailed Aug. 21, 2020.
Mendes et al. (2016) "Kinetics of arterial carbon dioxide during veno-venous extracorporeal membrane oxygenation support in an apnoeic porcine model," Intensive Care Medicine Experimental 4(1): 1-11.
Messai et al. 2013 (published online Dec. 5, 2012) "A New Formula For Determining Arterial Oxygen Saturation During Venovenous Extracorporeal Oxygenation," Intensive Care Medicine 39: 327-334.
Nassar et al. (Jun. 2017) "Estimating Arterial Partial Pressure of Carbon Dioxide in Ventilated Patients: How Valid Are Surrogate Measures?", American Thoracic Society 14(6): 1005-1014.
Nunes et al. (2014) "Severe Hypoxemia During Veno-Venous Extracorporeal Membrane Oxygenation: Exploring the Limits of Extracorporeal Respiratory Support", Clin 69(3): 173-178.
Romano et al. (2017) "Extracorporeal respiratory support in adult patients," Jornal Brasileiro de Pneumologia 43(1): 60-70.
Transonic Systems Inc. (2015) "Best Practices in Hemodialysis," Handbook: 80 pgs.
Walker et al. (2009) "Calculating Mixed Venous Saturation during Veno-Venous Extracorporeal Membrane Oxygenation," Perfusion 24(5): 333-339.
Dr. Cameron Troup MD, "SvO2: Definition, Normal Values, Clinical Use, Importance and Possible Problems", Aug. 15, 2022, Scopeheal https://web.archive.org/web/20220815160312/https://scopeheal/svo2/ (Year:2022).
"Circulatory system", Jun. 22, 2024, Britannica https://web.archive.org/web/20220815160312/https://scopeheal.com/svo2/https://www.britannica.com/science/circulatory-system/Vascular-systems (for easier acess of interactive diagram) (Year: 2024).

* cited by examiner

140

ARTERIAL
(DELIVERY)
CANNULA

SUPERIOR VENA
CAVA

30

142

RECIRCULATION

112

30

INFERIOR VENA
CAVA

VENOUS
(WITHDRAWAL)
CANNULA

110

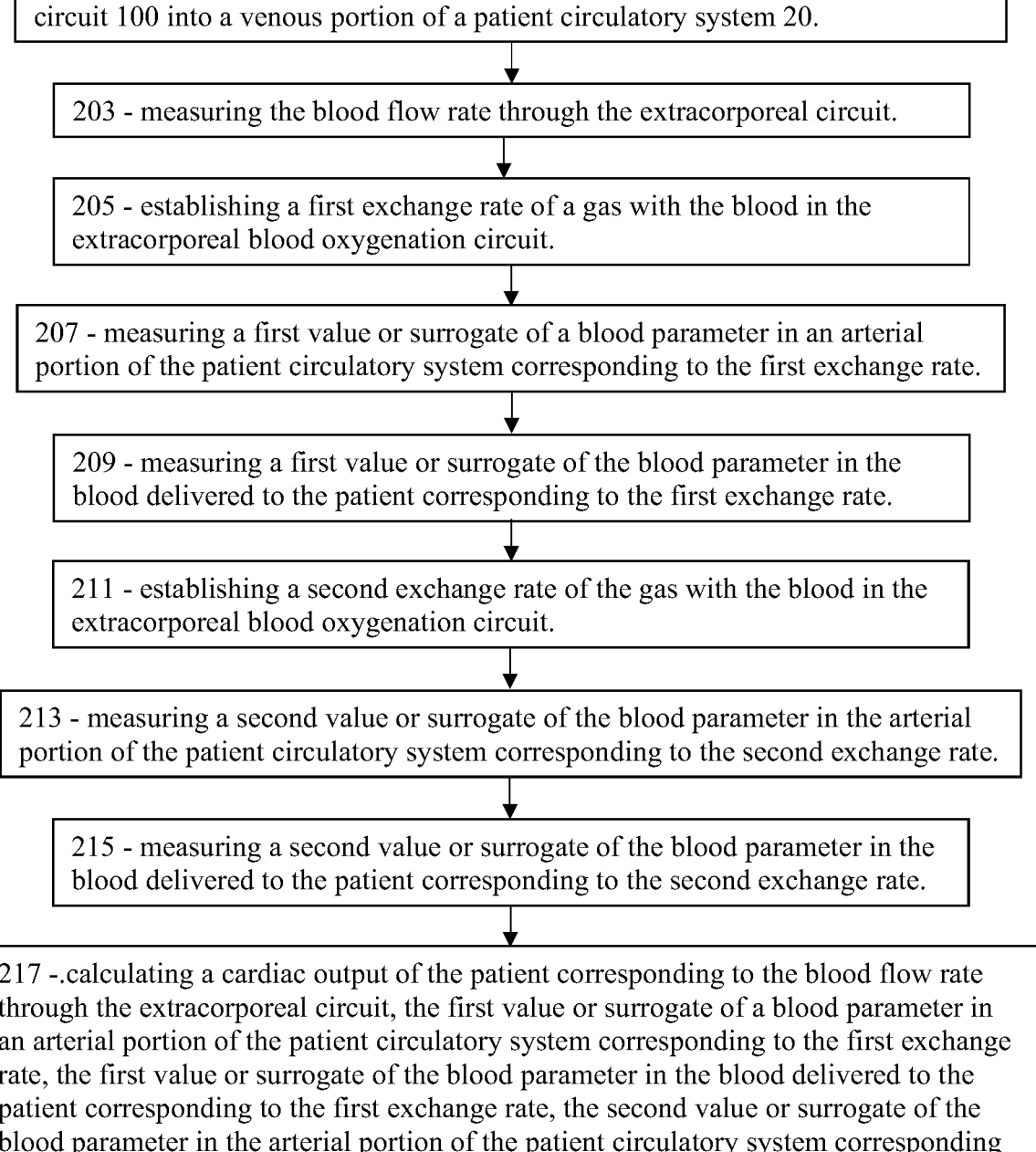

201 - establishing a blood flow rate from the extracorporeal blood oxygenation circuit 100 into a venous portion of a patient circulatory system 20.

203 - measuring the blood flow rate through the extracorporeal circuit.

205 - establishing a first exchange rate of a gas with the blood in the extracorporeal blood oxygenation circuit.

207 - measuring a first value or surrogate of a blood parameter in an arterial portion of the patient circulatory system corresponding to the first exchange rate.

209 - measuring a first value or surrogate of the blood parameter in the blood delivered to the patient corresponding to the first exchange rate.

211 - establishing a second exchange rate of the gas with the blood in the extracorporeal blood oxygenation circuit.

213 - measuring a second value or surrogate of the blood parameter in the arterial portion of the patient circulatory system corresponding to the second exchange rate.

215 - measuring a second value or surrogate of the blood parameter in the blood delivered to the patient corresponding to the second exchange rate.

217 -.calculating a cardiac output of the patient corresponding to the blood flow rate through the extracorporeal circuit, the first value or surrogate of a blood parameter in an arterial portion of the patient circulatory system corresponding to the first exchange rate, the first value or surrogate of the blood parameter in the blood delivered to the patient corresponding to the first exchange rate, the second value or surrogate of the blood parameter in the arterial portion of the patient circulatory system corresponding to the second exchange rate, and the second value or surrogate of the blood parameter in the blood delivered to the patient corresponding to the second exchange rate.

CALCULATING CARDIAC OUTPUT OF A PATIENT UNDERGOING VENO-VENOUS EXTRACORPOREAL BLOOD OXYGENATION

CROSS-REFERENCE TO RELATED APPLICATIONS

This application claims the benefit of U.S. provisional patent application 62/842,192 filed May 2, 2019, which disclosure is hereby expressly incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

STATEMENT REGARDING PRIOR DISCLOSURES BY THE INVENTOR OR A JOINT INVENTOR

Not applicable.

BACKGROUND OF THE INVENTION

The present disclosure relates to assessing cardiac output of a patient operably connected to a veno-venous (VV) extracorporeal circuit, and particularly to a veno-venous extracorporeal blood oxygenation circuit such as but not limited to a veno-venous extracorporeal membrane oxygenation (ECMO) circuit.

VV ECMO is a medical procedure employed in patients who are experiencing life-threatening respiratory failure, typically Acute Respiratory Distress Syndrome (ARDS). However, other indications include infection, such as viral, bacterial, fungus, PCP; primary lung disease, such as cystic fibrosis, hemorrhagic auto immune diseases; idiopathic fibrosis, sickle cell crisis, primary pulmonary hypertension; chest trauma, post pneumonectomy; post-transplant: acute, chronic (bronchiolitis obliterans); chronic respiratory failure bridging to transplant.

In these patients, blood that is passing the lungs is poorly oxygenated, and thus not enough oxygen is delivered to the tissue. This lack of oxygen delivery causes damage to the tissue and can ultimately the death of the patient. Extracorporeal blood oxygenation, such as VV ECMO, supplements or replaces blood oxygenation by the lungs of the patient.

In VV ECMO, large cannulas are inserted usually through femoral and/or jugular veins with the tip located in the superior and/or inferior vena cava or in the right atrium. These cannulae are then connected to an extracorporeal circuit which includes a pump and a membrane oxygenator. Blood is usually withdrawn from one (or two locations) and delivered close to the right atria, but there are multiple modifications. The patient blood is continuously circulated through the extracorporeal circuit, by being withdrawn from the patient, then circulated through an oxygenator, such as a membrane oxygenator, where the blood is then oxygenated. The blood is returned to the patient where the now oxygenated blood is pumped by right heart through lungs to left heart which delivers the oxygenated blood to the body tissue.

An important consequence of VV ECMO treatment is the occurrence of recirculation. Recirculation arises when a portion of the oxygenated blood that is being returned to the patient does not pass into the patient heart but is withdrawn into the extracorporeal circuit. This can occur due to poor positioning of the withdrawal and delivery cannulas, and/or if the patient has insufficient cardiac output to accept the full flow of oxygenated blood. Recirculation can be a problem during treatment, as the presence of recirculation means that some portion of the therapy being supplied to the patient is not actually assisting in their recovery.

The VV ECMO procedure is usually applied to patients that have a good working heart. During the course of VV ECMO, cardiac insufficiency (often of the right heart) may develop. This can be a life threatening situation. Sufficiency of circulation by the heart is typically assessed by measuring the cardiac output. Current standard methods to measure cardiac output (CO) such as pulmonary artery thermodilution and transpulmonary thermodilution are invasive as well as often inaccurate. In the VV ECMO setting, these methods may give misleading results, especially at high recirculation levels. As a result, a dramatic heart failure may be missed. An identified decrease in CO can be addressed by physicians either by medication therapy or by moving the patient to VA ECMO, where the extracorporeal circuit provides heart support in addition to lung support (though the VA ECMO is more invasive).

BRIEF SUMMARY OF THE INVENTION

Generally, the present disclosure provides a non-invasive method and apparatus to measure cardiac output, CO, in patients operably connected to a veno-venous extracorporeal circuit, and particularly a veno-venous extracorporeal blood oxygenation circuit such as but not limited to a veno-venous extracorporeal membrane oxygenation (ECMO) circuit.

In one configuration, the present disclosure provides a method for calculating cardiac output of a patient undergoing veno-venous extracorporeal blood oxygenation, wherein the method includes identifying a blood flow rate from an extracorporeal blood oxygenation circuit into a venous portion of a patient circulatory system; establishing a first removal rate of carbon dioxide from the blood in an oxygenator in the extracorporeal blood oxygenation circuit; determining (i) a first arterial carbon dioxide content or surrogate and (ii) a first carbon dioxide content or surrogate in the blood delivered to the patient after passing the oxygenator corresponding to the first removal rate of carbon dioxide from the blood; establishing a second removal rate of carbon dioxide from the blood in the oxygenator in the extracorporeal blood oxygenation circuit; determining (i) a second arterial carbon dioxide content or surrogate and (ii) a second carbon dioxide content or surrogate in the blood delivered to the patient after passing the oxygenator corresponding to the second removal rate of carbon dioxide from the blood; and calculating a cardiac output of the patient corresponding to the blood flow rate, the first arterial carbon dioxide content or surrogate, the first carbon dioxide content or surrogate in the blood delivered to the patient after passing the oxygenator corresponding to the first removal rate of carbon dioxide from the blood; the second arterial carbon dioxide content or surrogate and the second carbon dioxide content or surrogate in the blood delivered to the patient after passing the oxygenator corresponding to the second removal rate of carbon dioxide from the blood.

In a further configuration, the present disclosure provides a method for calculating cardiac output of a patient undergoing veno-venous extracorporeal blood oxygenation, wherein the method includes determining a blood flow rate from an extracorporeal blood oxygenation circuit into a venous portion of a patient circulatory system; establishing a first exchange rate of a gas with the blood in the extracorporeal blood oxygenation circuit; measuring a first value or surrogate of a blood parameter in an arterial portion of the patient circulatory system corresponding to the first exchange rate; measuring a first value or surrogate of the blood parameter in the blood delivered to the patient corresponding to the first exchange rate; establishing a second exchange rate of the gas with the blood in the extracorporeal blood oxygenation circuit; measuring a second value or surrogate of the blood parameter in the arterial portion of the patient circulatory system corresponding to the second exchange rate; measuring a second value or surrogate of the blood parameter in the blood delivered to the patient corresponding to the second exchange rate; and calculating a cardiac output of the patient corresponding to the blood flow rate, the first value or surrogate of a blood parameter in an arterial portion of the patient circulatory system corresponding to the first exchange rate, the first value or surrogate of the blood parameter in the blood delivered to the patient corresponding to the first exchange rate, the second value or surrogate of the blood parameter in the arterial portion of the patient circulatory system corresponding to the second exchange rate, and the second value or surrogate of the blood parameter in the blood delivered to the patient corresponding to the second exchange rate.

The present disclosure also provides an apparatus for quantifying a cardiac output of a patient operably connected to an extracorporeal blood oxygenation circuit, the extracorporeal blood oxygenation circuit having a venous line withdrawing blood from a circulatory system of the patient, a blood oxygenator, a pump and an arterial line returning oxygenated blood to a venous portion of the circulatory system, wherein the apparatus includes a controller configured to connect to one of the blood oxygenator and the pump, the controller configured to calculate a cardiac output of the patient based on a measured flow rate of oxygenated blood from the extracorporeal circuit, a first arterial carbon dioxide content or surrogate and a first carbon dioxide content or surrogate in the blood delivered to the patient circulatory system measured during a first flow rate of sweep gas though an oxygenator in the extracorporeal circuit; and a second arterial carbon dioxide content or surrogate and a second carbon dioxide content or surrogate in the blood delivered to the patient circulatory system measured during a second flow rate of sweep gas though the oxygenator in the extracorporeal circuit.

BRIEF DESCRIPTION OF THE SEVERAL VIEWS OF THE DRAWING(S)

FIG. 3 is a flow chart of a representative method of the present disclosure.

4

DETAILED DESCRIPTION OF THE INVENTION

Figure 1:
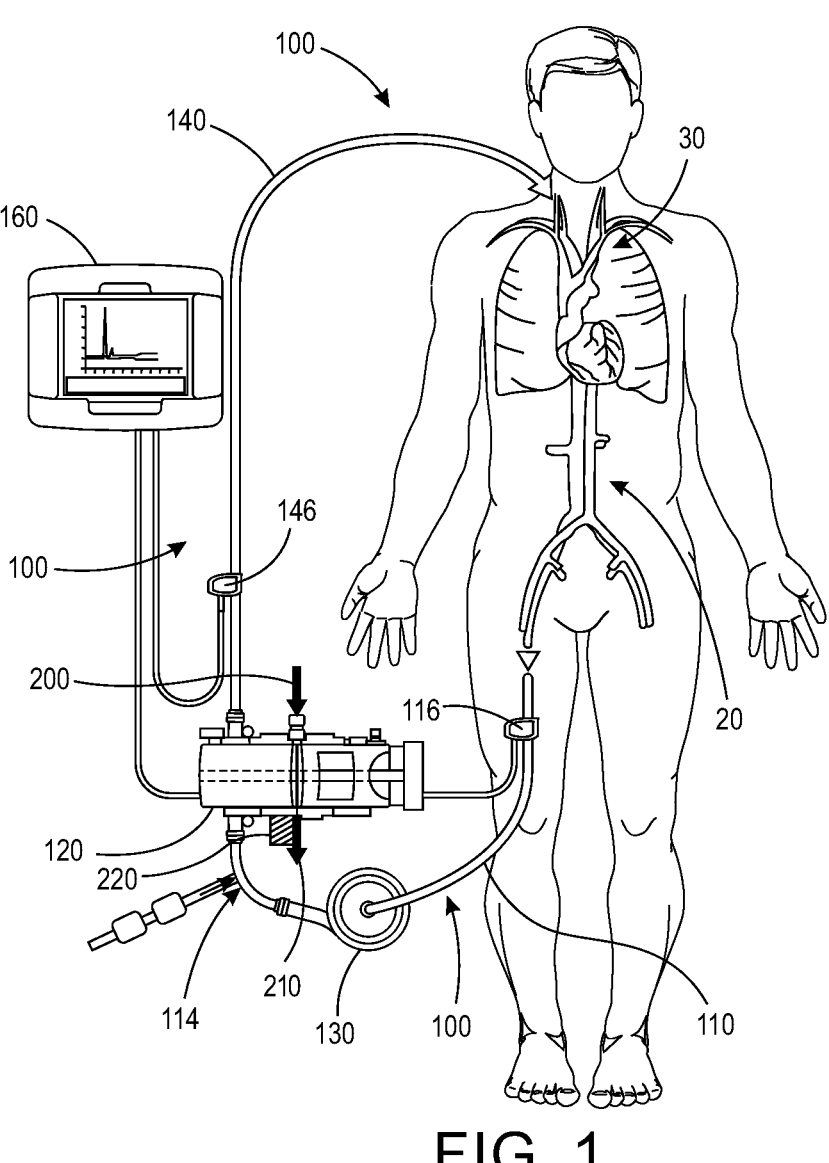
FIG. 1 is a representative veno-venous extracorporeal blood oxygenation circuit.

Referring to FIG. 1, an extracorporeal blood oxygenation circuit 100 is shown connected to a circulatory system 20 of patient 10.

The circulatory system 20 is a human (or animal) circulatory system including blood, a vascular system, and a heart. For purposes of this description, the circulatory system 20 is includes a cardiopulmonary system 30 and a systemic system connecting the cardiopulmonary system 30 to the tissues of the body. Specifically, the systemic system passes the blood though the vascular system (arteries, veins, and capillaries) throughout the body.

The cardiopulmonary system 30 includes the right heart, the lungs and the left heart, as well as the vascular structure connecting the right heart to the lungs, the lungs to the left heart and some portion of the aorta and large veins located between the extracorporeal circuit and the right and left heart. That is, in theory the cardiopulmonary system 30 would include only the right heart, the lungs, the left heart and the vascular structure directly connecting the right heart to the lungs and the lungs to the left heart. However, in practice it is sometimes impracticable to operably connect the extracorporeal circuit 100 immediately adjacent the large vein at the right heart. Therefore, the cardiopulmonary system 30 often includes a limited length of the vein entering the right heart. For example, the extracorporeal circuit 100 can be connected to a femoral vein, thereby effectively extending the cardiopulmonary system 30 to such femoral vein.

For cardiopulmonary and vascular systems, the term "upstream" of a given position refers to a direction against the flow of blood, and the term "downstream" of a given position is the direction of blood flow away from the given position. The "arterial" side or portion is that part in which oxygenated blood flows from the heart to the capillaries. The "venous" side or portion is that part in which blood flows from the capillaries to the heart and lungs (the cardiopulmonary system 30).

The basic components of the extracorporeal circuit 100 for a conventional extracorporeal oxygenation machine include a venous (or access) line 110, an oxygenator 120 and heat exchanger (not shown), a pump 130, an arterial line filter (not shown), an arterial (or return) line 140, a sensor 116 in the venous line, a sensor 146 in the arterial line and a controller 160.

The extracorporeal circuit 100 is configured to form a veno-venous (VV) extracorporeal circuit 100. In the veno-venous extracorporeal circuit 100, the site of the withdrawal of blood from the circulatory system 20 to the extracorporeal circuit 100 and the site of introduction of blood from the extracorporeal circuit to the circulation system both occur in the venous portion of the circulation system.

Thus, the VV extracorporeal circuit 100 withdraws blood from the venous portion of the circulatory system 20 (or cardiopulmonary system 30), and returns the blood to the venous portion of the circulation system. The withdrawn blood can be treated while it is withdrawn, such as through gas exchange or oxygenation (ECMO) before being returned to the venous portion of the circulatory system 20. The blood treatment can be any of a variety of treatments including, but not limited to, oxygenation (and carbon dioxide withdrawal).

The venous line 110 extends from the venous portion of the circulatory system 20, and preferably from a venous portion of the cardiopulmonary system 30. As seen in FIG.

2, the venous line 110 can include a venous cannula 112 providing the fluid connection to the circulatory system 20.

The venous line 110 can also include or provide an indicator introduction port 114 as the site for introducing an indicator into the extra corporeal circuit 100. In one configuration, the indicator introduction port 114 for introducing the dilution indicator is upstream to an inlet of the oxygenator 120. In selected configurations, the introduction site 114 can be integrated into the oxygenator 120.

It is also contemplated, that a component of the extracorporeal circuit 100 can be controlled to create or induce an indicator within the flow in the extracorporeal circuit. For example, as set forth below, a sweep gas rate in the oxygenator 120 can be changed, a filtration or treatment rate or heater can be sufficiently changed to create an effective indicator in the extracorporeal circuit 100 which then travels through the cardiopulmonary system 30.

In the venous line 110, the sensor 116, can be a dilution sensor for sensing passage of the indicator through the extracorporeal circuit 100. The dilution sensor 116 (as well as sensor 146) can be any of a variety of sensors, and can cooperate with the particular indicator. The sensor 116 (as well as sensor 146) can measure different blood properties: such as but not limited to temperature, Doppler frequency, electrical impedance, optical properties, density, ultrasound velocity, concentration of glucose, oxygen saturation and other blood substances (any physical, electrical or chemical blood properties). It is also understood the sensor 116 can also measure the blood flow rate. Alternatively, there can a sensor (not shown) in addition to sensor 116 be to measure the blood flow rate. Thus, in one configuration the present system includes a single blood property sensor and a single flow rate sensor. It is further contemplated that a single combined sensor for measuring flow rate and a blood parameter (property) can be used. As set forth herein, in some pumps 130, a rotational speed, RPM (rotations per minute) of the pump can be measured for providing a measurement of blood flow rate.

Figure 2:
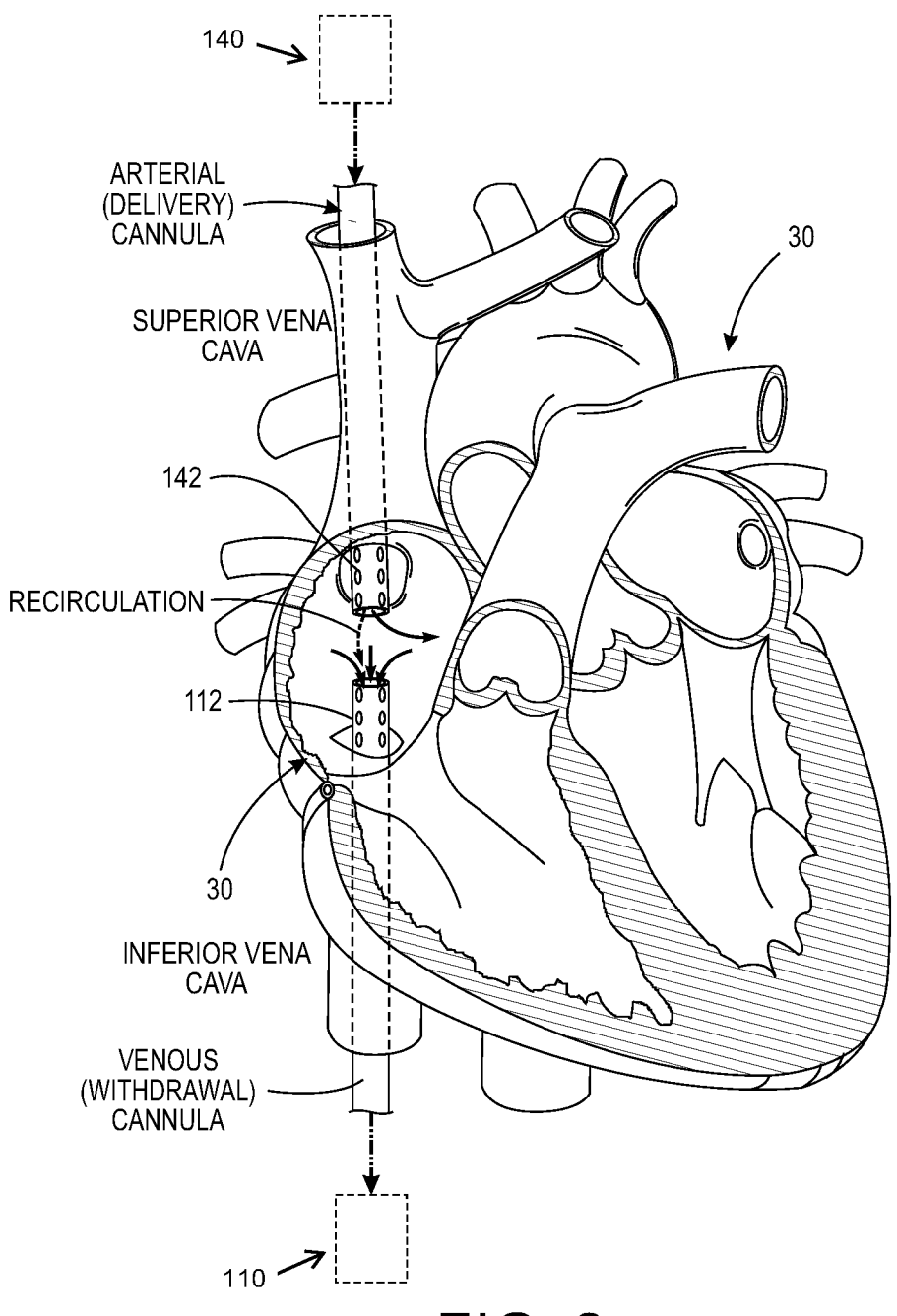
FIG. 2 is representation of the location of blood introduction and blood withdrawal in the veno-venous extracorporeal blood oxygenation circuit.

The arterial line 140 connects the extracorporeal circuit 100 to a venous portion of the circulatory system 20 and in one configuration to a venous portion of the cardiopulmonary system 30. The arterial line 140 usually connects to the superior vena cava but may connected to right atria (tip position) or inferior vena cava. As seen in FIG. 2, the arterial line 140 can include an arterial cannula 142 providing the fluid connection to the circulatory system 20. It is also understood that multi-lumen catheters can be used to provide VV ECMO.

However, it is understood the sensors 116, 146 can be located outside of the extracorporeal circuit. That is, the sensors 116, 146 can be remotely located and measure in the extracorporeal circuit 100, the changes produced in the blood from the indicator introduction or values related to the indicator introduction which can be transmitted or transferred by means of diffusion, electro-magnetic or thermo fields or by other means to the location of the sensor.

It is further understood that only one dilution sensor may be needed to measure recirculation by indicator dilution. While such resulting measurement of recirculation may be less accurate than recirculation measured with two sensors, it is recognized that only one flow sensor may be needed to perform cardiac output measurement.

The oxygenator 120 can be broadly classified into bubble type and oxygenators and membrane type oxygenators. The membrane type oxygenators fall under the laminate type, the coil type, and the hollow fiber type. Membrane type oxygenators offer advantages over the bubble type oxygenators as the membrane type oxygenators typically cause less blood damage, such as hemolysis, protein denaturation, and blood coagulation as compared with the bubble type oxygenators. Although the preferred configuration is set forth in terms of a membrane type oxygenator, it is understood any type of oxygenator can be employed.

The pump 130 can be any of a variety of pumps types, including but not limited to a roller (or impeller or centrifugal) pump. The pump 130 induces a blood flow rate through the extracorporeal circuit 100. Depending on the specific configuration, the pump 130 can be directly controlled at the pump or can be controller through the controller 160 to establish a given blood flow rate in the extracorporeal circuit. The pump 130 can be at any of a variety of locations in the extracorporeal circuit 100, and is not limited to the position shown in the Figures. In one configuration, the pump 130 is a commercially available pump and can be set or adjusted to provide any of a variety of flow rates wherein the flow rate can be read by a user and/or transmitted to and read by the controller 160.

The controller 160 is typically connectable to the oxygenator 120, the pump 130 and the sensor(s) 116, 146. The controller 160 can be a stand-alone device such as a personal computer, a dedicated device or embedded in one of the components, such as the pump 130 or the oxygenator 120. Although the controller 160 is shown as connected to the sensors 116 and 146, the pump 130 and the oxygenator 120, it is understood the controller can be connected to only the sensors, the sensors and the pump, or any combination of the sensors, pump and oxygenator. In one configuration, at least one of the pump 130 and the controller 160 provides for control of the pump and the flow rate of the blood through the pump, respectively. It is also understood, the controller 160 also can be connected to a pulse oximeter to automatically collect data or oximetry data can be put manually into the controller. Alternatively, the oximeter and the controller 160 can be integrated as a single unit.

The controller 160 is programmed with the equations as set forth herein and can perform the associated calculations based on inputs from the user or connected components.

The normal or forward blood flow through the extracorporeal circuit 100 includes withdrawing blood through the venous line 110 from the venous side circulatory system 20 (and particularly the cardiopulmonary circuit 30), passing the withdrawn blood through the extracorporeal circuit (to treat such as oxygenate), and introducing the withdrawn (or treated or oxygenated) blood through the arterial line 140 into the venous side of the circulation system, such as through the arterial cannula 142. The pump 130 thereby induces a blood flow at a known (measured) blood flow rate through the extracorporeal circuit 100 from the venous line 110 to the arterial line 140.

For purposes of the present description, the following terminology is used. Cardiac output CO is the amount of blood pumped out by the left ventricle in a given period of time (typically a 1 minute interval). The heart capacity (flow) is typically measured by cardiac output CO. The term blood flow rate means a rate of blood passage, volume per unit time. The blood flow rate is a volumetric flow rate ("flow rate"). The volumetric flow rate is a measure of a volume of liquid passing a cross-sectional area of a conduit per unit time, and may be expressed in units such as milliliters per min (ml/min) or liters per minute (1/min).

To provide blood oxygenation to the extracorporeal circuit 100, the extracorporeal circuit contains a blood oxygenator (oxygenator) 120. A sweep gas mixture of air and oxygen is delivered into the oxygenator 120 through an inlet

200 and exits through an outlet 210 (air pump not shown). The sweep gas flow rate can be changed, such as by a sweep gas regulator integral with or operably connected to the oxygenator 120. Carbon dioxide elimination from the blood by the oxygenator 120 depends on the sweep gas flow rate. That is, the rate of sweep gas flow through the membrane lung (oxygenator 120) determines the amount of blood decarboxylation.

The carbon dioxide content in the blood, ($SCO_2$) of blood leaving the oxygenator 120 through the outlet 210 ($S_{ecmo}CO_2$ below) is not materially affected by $Q_b$, but rather predominantly determined by the sweep gas flow rate in the oxygenator.

The value of carbon dioxide content in the blood, $S_{ecmo}CO_2$, can be directly measured or estimated via a surrogate by direct blood sampling (arterial blood gas analysis) or by a sensor 220 in the oxygenator outflow air 210 measuring carbon dioxide partial pressure. Any of the commercially available sensors for measuring the actual carbon dioxide, or a surrogate value, can be used. The surrogate is a value or measurement that is related to a $CO_2$ content which can include but is not limited to: the partial pressure of $CO_2$ in the gas, partial pressure of $CO_2$ dissolved in solution, the bicarbonate concentration of blood, and carbaminohemoglobin concentration. In general, it is assumed that use of a surrogate rather than the true content (actual parameter measurement) will be less accurate.

The purpose of the present system is to provide a simple noninvasive technology to measure CO in VV extracorporeal blood oxygenation, such as in a VV ECMO setting. To apply the present technique to measure cardiac output CO during VV extracorporeal blood oxygenation, including ECMO, the following terms are employed:

$S_vCO_2$—mixed venous carbon dioxide content (in venous vessels prior to entering the heart).

$S_aCO_2$—arterial carbon dioxide content, (which as set forth below can be measured or estimated via a surrogate, including but not limited to arterial blood sample (arterial blood gas analysis, ABG), arterialized capillary blood gas analysis; or partial pressure of transcutaneous carbon dioxide, as well as the carbon dioxide content in the ventilator or the patient's expired gases.

$S_{ecmo}CO_2$—carbon dioxide content in the blood delivered to the patient after passing the oxygenator 120, which as set forth herein can be directly measured from the blood passing to the patient or determined or calculated via a surrogate, such as carbon dioxide partial pressure from measurements of the sensors in the outflow of sweep gas air from the oxygenator.

$Q_b$—extracorporeal flow rate, (which as set forth below can be measured by a flow rate of a pump in the extracorporeal circuit or readily measured with commercially available flow meters).

R %—Recirculation (%)

CO—Cardiac output

Balance Equation No Recirculation

In the first instance, a mass balance equation is applied to the extracorporeal circuit 100. For this analysis, the assumptions are made (i) there is no recirculation present and (ii) the lungs are only negligibly exchanging $CO_2$ (in other words, the lungs are functioning poorly).

A mass balance equation for $CO_2$ content in blood can be written for VV ECMO:

$$Q_b \times S_{ecmo}CO_2 + (CO - Q_b) \times S_vCO_2 = CO \times S_aCO_2 \qquad \text{Eq. 1A}$$

Where $S_{ecmo}CO_2$, $S_vCO_2$ and $S_aCO_2$ are as set forth above.

In this and all following Equations, it is noted that values in this balance equation will be most accurate for poorly functioning lungs for which the extraction/exchange of carbon dioxide is compromised (minimal). If the lungs are partly working, this equation remains correct for carbon dioxide of blood flowing after lungs. In such situation, $S_vCO_2$ may need to be re-named, but the balance Equation remains the same.

Solving for CO:

$$Q_b \times S_{ecmo}CO_2 + CO \times S_vCO_2 - Q_b \times S_vCO_2 = CO \times S_aCO_2 \quad \text{Eq. 2A}$$

$$CO \times (S_aCO_2 - S_vCO_2) = Q_b \times (S_{ecmo}CO_2 - S_vCO_2) \qquad \text{Eq. 3A}$$

$$CO = Q_b \times \frac{(S_{ecmo}CO_2 - S_vCO_2)}{(S_aCO_2 - S_vCO_2)} \qquad \text{Eq. 4A}$$

Currently, during VV ECMO treatment, $Q_b$ and $S_{ecmo}CO_2$ can be measured or estimated from a surrogate, while $S_vCO_2$ is difficult to measure. That is, $S_vCO_2$ is typically measured by blood sampling pre-oxygenator (upstream) of the oxygenator 120 in extracorporeal (ECMO) circuit 100 which may be different from mixed venous value and is subject to the presence of any recirculation.

Thus, depending on the confidence in the $S_vCO_2$ value, there are 2 unknowns in Equation 4A, or the equation can still be used for CO assessment based on the present terms, but is less accurate.

Balance Equation with Recirculation

A further configuration of the present system can incorporate an accounting of any recirculation. In veno-venous extracorporeal blood oxygenation, such as VV ECMO, recirculation is the withdrawal of reinfused oxygenated blood through the drainage cannula (access line) without the reinfused oxygenated blood passing through the circulatory system 20. Because recirculated blood does not contribute to oxygen delivery in the circulatory system 20, the presence of recirculation decreases the efficiency of the extra-corporeal blood oxygenation (ECMO) procedure.

In case of recirculation, the actual effective flow, $Q_{eff}$, that carries 100% oxygenated blood into heart will be:

$$Q_{eff} = Q_b \times \left(1 - \frac{R\%}{100}\right) \qquad \text{Eq. 5A}$$

Replacing $Q_b$ with $Q_{eff}$ in Equation 4A, yields:

$$CO = Q_{eff} \frac{(S_{ecmo}CO_2 - S_vCO_2)}{(S_aCO_2 - S_vCO_2)} \qquad \text{Eq. 6A}$$

Substituting $Q_b$ for $Q_{eff}$ provides:

$$CO = Q_b \times \left(1 - \frac{R\%}{100}\right) \times \frac{(S_{ecmo}CO_2 - S_vCO_2)}{(S_aCO_2 - S_vCO_2)} \qquad \text{Eq. 7A}$$

Two Balance Equations with Recirculation

To increase the accuracy of the CO measurements with the purpose of eliminating the potentially unreliable or unknown value of $S_vCO_2$ and the lung influence, the flow rate of the sweep gas can be changed. This produces a different value of $S_{ecmo}CO_2$ which will change the arterial content of carbon dioxide, $S_aCO_2$ as well as any potentially exhaled $CO_2$.

An increase in the flow rate of the sweep gas (such as via the sweep gas flow rate of the oxygenator 120 and through the outlet 210) will decrease $S_{ecmo}CO_2$, and a decrease of the sweep gas flow rate will increases $S_{ecmo}CO_2$.

Thus, two equations can be produced analogous to Eq. 7A for two different sweep gas flow rates. In the two equation system (one equation for each sweep gas flow rate), index (1) and index (2) represent the first and second sweep gas flow rate, respectively. Upon considering that the changes in the $S_vCO_2$ and CO are negligible between the two different sweep gas flow rates, then:

$$CO = Q_b \times \left(1 - \frac{R\%}{100}\right) \times \frac{(S_{ecmo}CO_{2(1)} - S_vCO_2)}{(S_aCO_{2(1)} - S_vCO_2)} \qquad \text{Eq. 8A}$$

$$CO = Q_b \times \left(1 - \frac{R\%}{100}\right) \times \frac{(S_{ecmo}CO_{2(2)} - S_vCO_2)}{(S_aCO_{2(2)} - S_vCO_2)} \qquad \text{Eq. 9A}$$

The system of Equations 8A and 9A has two unknowns CO and $S_vCO_2$, thus can be solved for CO:

$$CO = Q_b \times \left(1 - \frac{R\%}{100}\right) \times \frac{(S_{ecmo}CO_{2(1)} - S_{ecmo}CO_{2(2)})}{(S_aCO_{2(1)} - S_aCO_{2(2)})} \qquad \text{Eq. 10A}$$

From Equation 10A, it can be seen that cardiac output, CO, can be measured from a known or measured single extracorporeal flow rate $Q_b$ in conjunction with a change in the sweep gas flow rate that provides a corresponding measured change in the (i) arterial carbon dioxide content, $S_aCO_2$, (which can be measured by arterial blood sample or estimated via a surrogate value of the patient's expired air) and (ii) the carbon dioxide content in the blood delivered to the patient after passing the oxygenator 120, $S_{ecmo}CO_2$, (which can be calculated or derived from measurement, such as direct measurement of the blood or via a surrogate from sensors in the outflow of sweep gas air from the oxygenator at each flow rate).

While the change in the sweep gas has been set forth as providing the change in carbon dioxide removal, it is understood that any other parameter change in blood passing to the patient from the extracorporeal circuit 100 can be used to measure CO in an analogous way to Eq. 8A-10A.

Further, as seen from Equation 8, if the recirculation, R %, is assumed or taken to be at or near zero, then Equation 10 reduces to:

$$CO = Q_b \times \frac{(S_{ecmo}CO_{2(1)} - S_{ecmo}CO_{2(2)})}{(S_aCO_{2(1)} - S_aCO_{2(2)})}. \qquad \text{Eq 11A}$$

where no measurement of recirculation is necessary to determine the cardiac output, CO.

Thus, in one configuration, the system includes the controller 160 operably connected to a carbon dioxide sensor 220 in the outflow of sweep gas from the oxygenator 120, from which $S_{ecmo}CO_2$ is measured from blood coming from oxygenator or estimated via a surrogate like carbon dioxide partial pressure. The controller 160 is also connected to a sensor or surrogate (such as arterial blood gas analysis, capnometer, expired air gas analysis, arterialized capillary blood gas analysis, or by measuring partial pressure of transcutaneous carbon dioxide) for determining the arterial carbon dioxide content $S_aCO_2$.

The controller 160 is programmed with or has access to a memory with lookup tables for converting a surrogate measurement to the respective carbon dioxide content as set forth above or a conversion of a surrogate measurement to the corresponding carbon dioxide content. In addition, the controller 160 is also connected to the pump 130, or a flow meter (not shown) for obtaining the flow rate through the extracorporeal circuit 100. The controller 160 is programmed with the present equations, or equivalents, for calculation of the cardiac output CO.

The present disclosure provides a method for calculating cardiac output of a patient undergoing veno-venous extracorporeal blood oxygenation, wherein the method includes the steps of establishing a blood flow rate from the extracorporeal blood oxygenation circuit 100 into a venous portion of a patient circulatory system 20; measuring the blood flow rate from the extracorporeal blood oxygenation circuit; establishing a first removal rate of carbon dioxide from the blood in the oxygenator 120 in the extracorporeal circuit 100; determining (i) a first arterial carbon dioxide content or a first surrogate of arterial carbon dioxide content and (ii) a first carbon dioxide content in the blood delivered to the patient after passing the oxygenator corresponding to the first removal rate of carbon dioxide from the blood (such as by measuring a first delivered carbon dioxide content or a first surrogate of carbon dioxide content in the blood delivered to the patient after passing the oxygenator corresponding to the first removal rate of carbon dioxide from the blood, such as measuring a surrogate to the first delivered carbon dioxide content); establishing a second removal rate of carbon dioxide from the blood in the oxygenator in the extracorporeal circuit; determining (i) a second arterial carbon dioxide content or a second surrogate of arterial carbon dioxide content and (ii) a second carbon dioxide content in the blood delivered to the patient after passing the oxygenator corresponding to the second removal rate of carbon dioxide from the blood (such as by measuring a second delivered carbon dioxide content or a second surrogate of carbon dioxide content in the blood delivered to the patient after passing the oxygenator corresponding to the second removal rate of carbon dioxide from the blood, such as measuring a surrogate to the second delivered carbon dioxide content); and calculating a cardiac output of the patient corresponding to the blood flow rate, the first arterial carbon dioxide content or surrogate, the first carbon dioxide content or surrogate (the first or surrogate delivered carbon dioxide content); the second arterial carbon dioxide content or surrogate and the second carbon dioxide content or surrogate (the second or surrogate delivered carbon dioxide content).

It is contemplated that establishing a first removal rate of carbon dioxide from the blood in the oxygenator 120 in the extracorporeal circuit 100 can include establishing a first sweep gas flow rate through the oxygenator. The method further contemplates measuring a recirculation in the extracorporeal blood oxygenation circuit 100 and adjusting the calculated cardiac output corresponding to the measured recirculation. In addition, measuring the blood flow rate can be provided by a pump in the extracorporeal blood oxygenation circuit 100. It is also understood a first dilution sensor can be connected to a venous line of the extracorporeal circuit 100 and a second dilution sensor connected to an arterial line of the extracorporeal circuit, wherein both sensors operably communicate with the controller. The method can include measuring recirculation by introducing an indicator into the extracorporeal circuit 100 upstream of the second dilution sensor and downstream of the first dilution sensor. As set forth above, it is understood that only one dilution sensor is required for recirculation measurement (but may be less accurate than employing two sensors), thus in select configurations only one flow sensor can be used for flow measurement.

Referring to FIG. 3, a further method for calculating cardiac output of a patient undergoing veno-venous extracorporeal blood oxygenation, includes the steps of 201—establishing a blood flow rate from the extracorporeal blood oxygenation circuit 100 into a venous portion of a patient circulatory system 20; step 203 measuring the blood flow rate through the extracorporeal circuit; step 205 establishing a first exchange rate of a gas with the blood in the extracorporeal blood oxygenation circuit; step 207 measuring a first value or surrogate of a blood parameter in an arterial portion of the patient circulatory system corresponding to the first exchange rate; step 209 measuring a first value or surrogate of the blood parameter in the blood delivered to the patient corresponding to the first exchange rate; step 211 establishing a second exchange rate of the gas with the blood in the extracorporeal blood oxygenation circuit; step 213 measuring a second value or surrogate of the blood parameter in the arterial portion of the patient circulatory system corresponding to the second exchange rate; step 215 measuring a second value or surrogate of the blood parameter in the blood delivered to the patient corresponding to the second exchange rate; and step 217 calculating a cardiac output of the patient corresponding to the blood flow rate through the extracorporeal circuit, the first value or surrogate of a blood parameter in an arterial portion of the patient circulatory system corresponding to the first exchange rate, the first value or surrogate of the blood parameter in the blood delivered to the patient corresponding to the first exchange rate, the second value or surrogate of the blood parameter in the arterial portion of the patient circulatory system corresponding to the second exchange rate, and the second value or surrogate of the blood parameter in the blood delivered to the patient corresponding to the second exchange rate. It is understood steps 201 and 203 can be combined into a single step of establishing predetermined blood flow rate from the extracorporeal blood oxygenation circuit 100 into a venous portion of a patient circulatory system 20.

In this method the measured value or surrogate blood parameter can be carbon dioxide. The method can further include measuring a recirculation in the extracorporeal blood oxygenation circuit 100 and adjusting the calculated cardiac output corresponding to the measured recirculation. In addition, measuring the blood flow rate in the extracorporeal blood oxygenation circuit can be provided by the pump in the extracorporeal blood oxygenation circuit. In one configuration, the method can further include operably connecting a first dilution sensor to a venous line of the extracorporeal blood oxygenation circuit and a second dilution sensor to an arterial line of the extracorporeal blood oxygenation circuit, and wherein measuring a recirculation includes introducing an indicator into the extracorporeal blood oxygenation circuit upstream of the second dilution sensor and downstream of the first dilution sensor. The method can further include measuring the first value of the blood parameter in the blood delivered to the patient corresponding to the first exchange rate prior to the blood entering the patient circulatory system, and measuring the second value of the blood parameter in the blood delivered to the patient corresponding to the second exchange rate prior to the blood entering the patient circulatory system.

In a further configuration, a method is provided for calculating cardiac output of a patient undergoing veno-venous extracorporeal blood oxygenation, the method including measuring a blood flow rate from an extracorporeal blood oxygenation circuit into a venous portion of a patient circulatory system; measuring (i) a first arterial carbon dioxide content and (ii) a first carbon dioxide content in blood delivered to the patient after passing the extracorporeal blood oxygenation circuit corresponding to a first removal rate of carbon dioxide from the blood in the extracorporeal blood oxygenation circuit; measuring (i) a second arterial carbon dioxide content and (ii) a second carbon dioxide content in the blood delivered to the patient after passing the extracorporeal blood oxygenation circuit corresponding to a second removal rate of carbon dioxide from the blood in the extracorporeal blood oxygenation circuit; and calculating a cardiac output of the patient corresponding to the measured blood flow rate, the first arterial carbon dioxide content, the first carbon dioxide content in the blood delivered to the patient after passing the oxygenator corresponding to the first removal rate of carbon dioxide from the blood in the extracorporeal blood oxygenation circuit; the second arterial carbon dioxide content and the second carbon dioxide content in the blood delivered to the patient after passing the oxygenator corresponding to the second removal rate of carbon dioxide from the blood in the extracorporeal blood oxygenation circuit. It is contemplated the first removal rate of carbon dioxide from the blood in an oxygenator in the extracorporeal blood oxygenation circuit includes establishing a first sweep gas flow rate through the oxygenator.

In yet another configuration, a method is provided for calculating cardiac output of a patient undergoing veno-venous extracorporeal blood oxygenation, the method including measuring a blood flow rate from an extracorporeal blood oxygenation circuit into a venous portion of a patient circulatory system; measuring a first value of a blood parameter in an arterial portion of the patient circulatory system corresponding to a first exchange rate of a gas with the blood in the extracorporeal blood oxygenation circuit; measuring a first value of the blood parameter in the blood delivered to the patient corresponding to the first exchange rate of a gas with the blood in the extracorporeal blood oxygenation circuit; measuring a second value of the blood parameter in the arterial portion of the patient circulatory system corresponding to a second exchange rate of the gas with the blood in the extracorporeal blood oxygenation circuit; measuring a second value of the blood parameter in the blood delivered to the patient corresponding to the second exchange rate of the gas with the blood in the extracorporeal blood oxygenation circuit; and calculating a cardiac output of the patient corresponding to the blood flow rate, the first value or surrogate of a blood parameter in an arterial portion of the patient circulatory system corresponding to the first exchange rate of the gas with the blood in the extracorporeal blood oxygenation circuit, the first value of the blood parameter in the blood delivered to the patient corresponding to the first exchange rate of the gas with the blood in the extracorporeal blood oxygenation circuit, the second value of the blood parameter in the arterial portion of the patient circulatory system corresponding to the second exchange rate of the gas with the blood in the extracorporeal blood oxygenation circuit, and the second value of the blood parameter in the blood delivered to the patient corresponding to the second exchange rate of the gas with the blood in the extracorporeal blood oxygenation circuit.

The present disclosure also contemplates an apparatus for quantifying a cardiac output of a patient operably connected to an extracorporeal blood oxygenation circuit, the extracorporeal blood oxygenation circuit having a venous line withdrawing blood from a circulatory system of the patient, a blood oxygenator, a pump and an arterial line returning oxygenated blood to a venous portion of the circulatory system, wherein the apparatus includes (a) a controller configured to connect to one of the blood oxygenator and the pump, the controller configured to calculate a cardiac output of the patient based on a measured first flow rate of oxygenated blood from the extracorporeal circuit, a first arterial carbon dioxide content or surrogate delivered to the patient circulatory system and a first carbon dioxide content or surrogate measured during a first flow rate of sweep gas though an oxygenator in the extracorporeal circuit; and a second arterial carbon dioxide content or surrogate and a second carbon dioxide content or surrogate delivered to the patient circulatory system measured during a second flow rate of sweep gas though the oxygenator in the extracorporeal circuit.

It is understood as used herein, the indicator is any substance that alters a measurable blood property. The indicator may alter any measurable parameter of the blood. For example, the indicator may be chemical, optical, electrical, thermal or any combination thereof. The particular indicator is at least partly dictated by the anticipated operating environment. Available indicators include saline solutions, increased or decreased temperature as well as dyes and various isotopes. The use of temperature differentials may be accomplished by locally creating a heat source (such as a heater in the oxygenator 120) or a heat sink in the surrounding flow. The creation of a local temperature gradient offers the benefit of being able to employ a dilution indicator without introducing any additional volume into the blood flow. That is, a temperature differential may be created without an accompanying introduction of a volume of indicator. Alternatively, a volume of heated or cooled blood may be introduced at the indicator introduction port 114 as the indicator. It is also contemplated, that a component of the extracorporeal circuit 100 can be controlled to create or induce an indicator within the flow in the extracorporeal circuit. For example, a filtration or treatment rate or heater can be sufficiently changed to create an effective indicator in the extracorporeal circuit 100 which then travels through the cardiopulmonary system 30.

For purposes of description, the term calculate (or calculating) means to determine the amount or number of something mathematically, including to evaluate or estimate the nature, amount or quantity.

For purposes of description, the term measure (or measuring) means how much there is of the relevant parameter, including ascertain or establish the size, amount, or degree of (something) such as by using an instrument or device marked in standard units or by comparing it with an object of known size, wherein the measuring may be of representative or a surrogate value or a surrogate parameter. For example, for measuring the oxygenated blood flow rate introduced into the patient circulation system 20, the setting of the pump 130 can be used, a separate flow meter can be used, or dilution measurement can be used. It is further contemplated that measuring can include a calculating step or steps.

As used herein, the term calculate or calculating means to discover or identify a number or an amount using mathematics, a mathematical processes or equations.

As used herein, the term surrogate is a parameter which is used as a metric for one or more other parameters. For purposes of description, when a specific parameter is recited as measured, it is understood that such measurement includes a representative of the parameter or a surrogate or surrogate parameter that is measured, without deviating from the present system. Thus, it is understood that measuring a parameter, flow rate, blood flow rate, recirculation or carbon dioxide content encompasses measuring the relevant representative parameter as well as measuring a surrogate or surrogate parameter.

This disclosure has been described in detail with particular reference to an embodiment, but it will be understood that variations and modifications can be effected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for quantifying a cardiac output of a patient operably connected to an extracorporeal blood oxygenation circuit, the extracorporeal blood oxygenation circuit having a venous line withdrawing blood from a circulatory system of the patient, a blood oxygenator, a pump, and an arterial line returning oxygenated blood to a venous portion of the circulatory system, the apparatus comprising:

(a) a controller configured to connect to one of the blood oxygenator and the pump, the controller configured to calculate a cardiac output of the patient based on a first flow rate of oxygenated blood from the extracorporeal blood oxygenation circuit, a first arterial carbon dioxide content corresponding to a first gas removal rate in the blood oxygenator in the extracorporeal blood oxygenation circuit, a first carbon dioxide content of the blood delivered to the patient circulatory system corresponding to the first gas removal rate in the blood oxygenator in the extracorporeal blood oxygenation circuit; and a first mixed venous carbon dioxide content corresponding to the first gas removal rate in the blood oxygenator in the extracorporeal blood oxygenation circuit.

2. The apparatus of claim 1, wherein the first arterial carbon dioxide content comprises one of a representative parameter and a surrogate of the first arterial carbon dioxide content.

3. The apparatus of claim 1, wherein the first carbon dioxide content of the blood delivered to the patient circulatory system comprises one of a representative parameter and a surrogate of the first carbon dioxide content of the blood delivered to the patient circulatory system.

4. The apparatus of claim 1, wherein the first mixed venous carbon dioxide content comprises one of a representative parameter and a surrogate of the first mixed venous carbon dioxide content.

5. The apparatus of claim 1, wherein the first flow rate of oxygenated blood from the extracorporeal blood oxygenation circuit comprises one of a representative parameter and a surrogate of the first flow rate of oxygenated blood from the extracorporeal blood oxygenation circuit.

6. The apparatus of claim 1, wherein the first mixed venous carbon dioxide content corresponding to the first gas removal rate in the blood oxygenator in the extracorporeal blood oxygenation circuit comprises a first mixed venous carbon dioxide content in a venous vessel prior to entering the heart, corresponding to the first gas removal rate in the blood oxygenator in the extracorporeal blood oxygenation circuit.

7. The apparatus of claim 1, wherein the controller calculates the cardiac output corresponding to the relationship $$CO = Q_b \times \frac{(S_{ecmo}CO_2 - S_vCO_2)}{(S_aCO_2 - S_vCO_2)},$$

where CO is the cardiac output, $Q_b$ is the first flow rate of oxygenated blood from the extracorporeal blood oxygenation circuit, $S_aCO_2$ is the first arterial carbon dioxide content corresponding to the first gas removal rate in the blood oxygenator in the extracorporeal blood oxygenation circuit, $S_{ecmo}CO_2$ is the carbon dioxide content of the blood delivered to the patient circulatory system corresponding to the first gas removal rate in the blood oxygenator in the extracorporeal blood oxygenation circuit, and $S_vCO_2$ is the first mixed venous carbon dioxide content corresponding to the first gas removal rate in the blood oxygenator in the extracorporeal blood oxygenation circuit.

8. The apparatus of claim 1, wherein the controller is further configured to calculate the cardiac output corresponding to a recirculation of oxygenated blood in the first flow rate into the venous line before passing through the circulatory system of the patient.

9. The apparatus of claim 1, wherein the controller is further configured to calculate the cardiac about corresponding to the relationship

16

$$CO = Q_b \times \left(1 - \frac{R\%}{100}\right) \times \frac{(S_{ecmo}CO_2 - S_vCO_2)}{(S_aCO_2 - S_vCO_2)},$$

where CO is the cardiac output, $Q_b$ is the first flow rate of oxygenated blood from the extracorporeal blood oxygenation circuit, $S_aCO_2$ is the first arterial carbon dioxide content corresponding to the first gas removal rate in the blood oxygenator in the extracorporeal blood oxygenation circuit, $S_{ecmo}CO_2$ is the first carbon dioxide content of the blood delivered to the patient circulatory system corresponding to the first gas removal rate in the blood oxygenator in the extracorporeal blood oxygenation circuit, $S_vCO_2$ is the first mixed venous carbon dioxide content corresponding to the first gas removal rate in the blood oxygenator in the extracorporeal blood oxygenation circuit, and R % is the recirculation of oxygenated blood in the first flow rate into the venous line before passing through the circulatory system of the patient.

10. The apparatus of claim 9, wherein the first mixed venous carbon dioxide content corresponding to the first gas removal rate in the blood oxygenator in the extracorporeal blood oxygenation circuit comprises a mixed venous carbon dioxide content in a venous vessel prior to entering the heart, corresponding to the first gas removal rate in the blood oxygenator in the extracorporeal blood oxygenation circuit.

* * * * *